(12) United States Patent
Maselli et al.

(10) Patent No.: US 9,625,383 B2
(45) Date of Patent: Apr. 18, 2017

(54) SENSOR ARRANGEMENT FOR MEASURING THE CONCENTRATION OF A SUBSTANCE

(71) Applicant: Tetra Laval Holdings & Finance S.A., Pully (CH)

(72) Inventors: Andrea Maselli, Parma (IT); Bo Runnberg, Smedstorp (SE); Eugenio Sighinolfi, Modena (IT); Hans Hallstadius, Lund (SE); Sylvain Debaecker, Eslöv (SE)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 26 days.

(21) Appl. No.: 14/387,638

(22) PCT Filed: Mar. 14, 2013

(86) PCT No.: PCT/EP2013/055200
§ 371 (c)(1),
(2) Date: Sep. 24, 2014

(87) PCT Pub. No.: WO2013/143859
PCT Pub. Date: Oct. 3, 2013

(65) Prior Publication Data
US 2015/0049335 A1    Feb. 19, 2015

(30) Foreign Application Priority Data

Mar. 27, 2012 (SE) .................................. 1250297
Jun. 13, 2012 (SE) .................................. 1250616

(51) Int. Cl.
*G01N 21/59* (2006.01)
*G01N 1/40* (2006.01)
(Continued)

(52) U.S. Cl.
CPC ............... *G01N 21/59* (2013.01); *B65B 3/04* (2013.01); *B65B 55/10* (2013.01); *G01N 1/40* (2013.01);
(Continued)

(58) Field of Classification Search
CPC ...... G01N 21/59; G01N 21/356; G01N 21/27; G01N 21/3159; G01N 1/40; G01N 2201/0696; B65B 55/10; B65B 3/04
(Continued)

(56) References Cited

U.S. PATENT DOCUMENTS 3,895,233 A    7/1975    Boll et al.
4,383,181 A    5/1983    Roess et al.
(Continued)

FOREIGN PATENT DOCUMENTS

CN    101122566 A    2/2008
CN    101413877 A    4/2009
(Continued)

OTHER PUBLICATIONS

International Search Report in PCT/EP2013/055200, mailed Jun. 27, 2013 (3 pages).
(Continued)

*Primary Examiner* — Sang Nguyen
(74) *Attorney, Agent, or Firm* — Finnegan, Henderson, Farabow, Garrett & Dunner, L.L.P.

(57) ABSTRACT

A sensor arrangement for determining a concentration of a substance in an open sample in the presence of an interfering material is disclosed. The sensor arrangement comprises a first light source emitting pulsed light at a first wavelength being absorbed by said substance, a second light source emitting pulsed light at a second wavelength being transmitted through said substance, optical means for directing at least a part of the emitted pulsed light of said first and second (Continued)

wavelengths through the open sample along the same optical path, and a sample detector arranged at an end of the optical path for receiving the emitted light of said first and second wavelengths being transmitted through the sample. The interfering material is formed as deposits on at least one of said optical means being exposed to said substance, and said first wavelength and said second wavelength are absorbed by said interfering material.

19 Claims, 3 Drawing Sheets

(51) Int. Cl.
    *B65B 55/10*     (2006.01)
    *G01N 21/25*     (2006.01)
    *G01N 21/27*     (2006.01)
    *G01N 21/31*     (2006.01)
    *B65B 3/04*     (2006.01)

(52) U.S. Cl.
    CPC ........... *G01N 21/256* (2013.01); *G01N 21/27* (2013.01); *G01N 21/3151* (2013.01); *G01N 2201/0696* (2013.01)

(58) Field of Classification Search
    USPC ...... 356/432–444, 246; 250/373, 395, 458.1, 250/226, 343, 339.13
    See application file for complete search history.

(56) References Cited

U.S. PATENT DOCUMENTS

| | | | |
|---|---|---|---|
| 4,471,220 A * | 9/1984 | Perry | G01N 21/39 250/338.5 |
| 4,749,276 A | 6/1988 | Bragg et al. | |
| 5,227,636 A | 7/1993 | Schwiesow | |
| 5,818,598 A * | 10/1998 | Kebabian | G01N 21/3518 356/434 |
| 6,665,061 B1 | 12/2003 | Abou-Saleh et al. | |
| 6,775,001 B2 * | 8/2004 | Friberg | G01J 3/42 356/432 |
| 6,841,778 B1 | 1/2005 | Shifflett et al. | |
| 7,323,687 B2 * | 1/2008 | Nanko | G01N 21/37 250/339.13 |
| 2002/0050567 A1 | 5/2002 | Boudet et al. | |
| 2003/0025909 A1 | 2/2003 | Hallstadius | |
| 2003/0107739 A1 * | 6/2003 | Lehmann | G01J 3/42 356/437 |
| 2005/0226548 A1 * | 10/2005 | Durkin | G01N 21/31 385/12 |
| 2006/0263253 A1 | 11/2006 | Steuerwald et al. | |
| 2007/0023334 A1 * | 2/2007 | Hallstadius | A61M 1/1656 210/94 |
| 2008/0024779 A1 * | 1/2008 | Aasmul | G01J 3/4406 356/317 |
| 2008/0285032 A1 * | 11/2008 | Ohkubo | G01N 15/0205 356/343 |
| 2009/0101822 A1 | 4/2009 | Mitra et al. | |
| 2010/0053621 A1 | 3/2010 | Olson et al. | |
| 2011/0248178 A1 * | 10/2011 | Haffner | G01N 21/3103 250/373 |
| 2012/0140229 A1 * | 6/2012 | Svanberg | G01N 21/1702 356/437 |
| 2014/0264077 A1 * | 9/2014 | Tokhtuev | G01N 21/59 250/458.1 |

FOREIGN PATENT DOCUMENTS

| | | |
|---|---|---|
| CN | 201555799 U | 8/2010 |
| CN | 201637666 U | 11/2010 |
| EP | 0762107 | 3/1997 |
| EP | 0916937 | 5/1999 |
| JP | 50-017275 | 6/1975 |
| JP | 62201334 | 9/1987 |
| JP | 01-244341 | 9/1989 |
| JP | 09-318528 | 12/1997 |
| JP | 2000-171394 | 6/2000 |
| JP | 4034920 | 6/2000 |
| JP | 2002-543382 | 12/2002 |
| JP | 2006-029968 | 2/2006 |
| JP | 2008-157874 | 7/2008 |
| JP | 2012-002067 | 1/2012 |
| WO | WO 2010/072270 A1 | 7/2010 |
| WO | WO 2010/095472 A1 | 8/2010 |
| WO | WO 2011/073789 | 6/2011 |

OTHER PUBLICATIONS

International Search Report in Swedish Application No. 1250616-8, mailed Dec. 12, 2012 (6 pages).

* cited by examiner

US 9,625,383 B2

SENSOR ARRANGEMENT FOR MEASURING THE CONCENTRATION OF A SUBSTANCE

CROSS-REFERENCE TO RELATED APPLICATIONS

This is a U.S. National Phase of PCT/EP2013/055200, filed Mar. 14, 2013, which claims the benefit of priority to Swedish Patent Application No. 1250297-7, filed Mar. 27, 2012, and Swedish Patent Application No. 1250616-8, filed Jun. 13, 2012, which are incorporated herein by reference.

TECHNICAL FIELD

The present invention relates to a sensor arrangement. More particularly, the present invention relates to a sensor arrangement for measuring the concentration of sterilizing substance within a sterilizing unit of a filling machine.

BACKGROUND

Different sensors for determining the amount, presence, or concentration of substances are well known and widely used within different industries in order to monitor and control physical parameters of a particular environment.

Since different applications require the use of specially designed sensors there is a vast amount of different sensing technologies commercially available.

One such sensing technology involves the use of light, wherein the sensor determines the amount of absorbance and/or transmittance through a sample being arranged in the optical path of the emitted light. Hence, such sensor arrangement typically involves a light source arranged on a first side of the sample, a detector arranged on the opposite side of the sample, and a controller for determining the absorbance and/or transmittance. Preferably, the controller also includes a calculating unit for converting the detected transmittance and/or absorbance into a quantity of the sample, such as the amount of a particular substance within the sample.

Examples of prior art light sensors are described in U.S. Pat. No. 3,895,233 and in EP0762107.

Light sensors are very attractive since they can be used for many different samples. The light absorbance spectrum of a substance is normally a complex curve why significant sensor resolution may be obtained by choosing a specific wavelength of the light used.

In food processing, such as liquid food packaging, carton-based packaging material is folded to a package whereafter it is filled with liquid food product. For complying with national safety regulations, but also to assure the quality of the enclosed food product, it is necessary to assure that the enclosed food product is sterilized. However, sterilization must also be provided for the package itself before being filled and sealed.

In modern filling machines the packaging material is normally sterilized by hydrogen peroxide ($H_2O_2$). The sterilization may either occur in a $H_2O_2$ sterilization chamber through which the packaging material is transported, or as a spray unit which provides a $H_2O_2$ gas into semi-finished packages prior to filling and sealing. Hence, there is a sterile zone through which the packaging material passes before filling.

The light absorbance spectrum of $H_2O_2$ has proven to be suitable for light sensors for detecting and measuring the amount of $H_2O_2$ in the sterile zone of the filling machine. Such light sensors also require the use of optical lenses and windows in order to direct the light through the $H_2O_2$ and to the detector. However, in gaseous environments such as the sterile zone of a liquid food filling machine deposits on the optical components have contributed to an increased noise in the measurements, thus reducing the quality of the measurements.

Although the above described sensor arrangements provide some advantages the complete construction of such sensor arrangement is not suitable in specific applications where interfering material tend to form deposits in the optical path.

Hence, there is a need for an improved sensor arrangement, especially for applications where it is of crucial importance to measure the amount of sterilizing substances within a sample.

SUMMARY

Accordingly, the present invention preferably seeks to mitigate, alleviate or eliminate one or more of the above-identified deficiencies in the art and disadvantages singly or in any combination and solves at least the above mentioned problems by providing a system according to the appended claims.

An object of the present invention is to allow the emitted light of the different wavelengths to follow the same optical path through the sample and to the sample detector.

A further object of the invention is to reduce the amount of electrical cables of the sensor arrangement.

A yet further object is to improve the quality of the sensor arrangement by reducing the risk of reactive substances, such as $H_2O_2$, coming into direct contact with the electronic components.

An idea of the invention is to therefore to emit light in a pulsed manner such that a single sample detector may detect the emitted light beams in a sequential order whereby the first and second light beams may follow the identical optical path through the sample to the sample detector.

A further idea is to provide a sensor arrangement which is insensitive for interfering material formed as deposits on various optical components arranged in the optical path of the emitted light.

According to an aspect, a sensor arrangement for determining the concentration of a substance in an open sample in the presence of an interfering material is provided. The sensor arrangement comprises a first light source emitting pulsed light at a first wavelength being absorbed by said substance, a second light source emitting pulsed light at a second wavelength being transmitted through said substance, optical means for directing at least a part of the emitted pulsed light of said first and second wavelength through the open sample along the same optical path, and a sample detector arranged at the end of the optical path for receiving the emitted light of said first and second wavelength being transmitted through the sample, wherein said interfering material is formed as deposits on at least one of said optical means being exposed to said substance, and wherein said first wavelength and said second wavelength is absorbed by said interfering material.

According to another aspect of the invention, a sensor arrangement for determining the concentration of a substance in a sample in the presence of an interfering material is provided. The sensor arrangement comprises a first light source emitting pulsed light at a first wavelength being absorbed by said substance and by said interfering material, a second light source emitting pulsed light at a second wavelength being transmitted through said substance and absorbed by said interfering material, optical means for directing at least a part of the emitted pulsed light of said first and second wavelength through the sample along the same optical path, and a sample detector arranged at the end of the optical path for receiving the emitted light of said first and second wavelength being transmitted through the sample.

The first light source, the second light source, and the sample detector may be arranged on the same side of the sample. This is advantageous in that the sensor arrangement may be made less bulky, and further in that a less amount of cables are necessary since the sample detector is positioned close to the controller.

The sensor arrangement may further comprise a reference detector for receiving a part of the emitted light of said first and second wavelength not being transmitted through the sample. Hence, the quality of the measurements may be improved since the reference detector will provide exact measurements of the emitted light before being transmitted through the sample.

The reference detector is arranged on the same side of the sample as the first light source, the second light source, and the sample detector. This further improves the compactness of the sensor arrangement.

The sensor arrangement may further comprise a controller being connected to the first light source, the second light source, the sample detector, and the reference detector and being configured to activate the first light source and the second light source in a pulsed sequence, said controller being further configured to associate a received signal of the sample detector and the reference detector with the associated light source. This is particularly advantageous in that the sample detector may be implemented as a single detector instead of separate sample detectors for each wavelength.

The controller may be further configured to associate the received signal of the sample detector and the reference detector as background light at occasions where none of the first light source and the second light source is activated. Hence, improved accuracy may be obtained since background noise may be subtracted from the received signals of the sample detector and the reference detector when the light sources are activated.

The first light source may be a UV-LED, whereby robust, small, reliable, and less expensive equipment are used.

Said controller may be configured to control the temperature of the first light source and the second light source. This is advantageous in that improved life time of the light sources may be achieved, as well as for reducing variations in light intensity and wavelength distribution.

The first light source, the second light source, the sample detector, and the reference detector may be enclosed in a first housing sealed from the sample. This makes the sensor arrangement particularly suitable for corrosive environments, such as hydrogen peroxide containing samples.

The first housing may comprise a first optical window for allowing light emitted from the first light source and the second light source to exit the first housing and enter the sample, and a second optical window for allowing the light emitted from the first light source and the second light source to exit the sample and enter the first housing, wherein said sensor arrangement further comprises a heater configured to increase the temperature of the first and second optical window. By providing the heater a reduced risk of condensation of sample substance is achieved. Further to this, by heating the optical windows there is less risk of stabilizer deposits which may affect the accuracy of the measurements.

Said first housing may comprise a cooler for reducing the temperature within the first housing. It may thus be possible to have lights sources close to power electronics whereby the size of the sensor may be reduced.

Said controller may be connected to a memory storing reference values for the received detector signals, and wherein the controller is further configured to transmit an alarm signal if a received detector signals differs from the stored reference values. This is preferred in situations where there is a risk that the optical windows may be damaged. In case of such damages the detected light intensities will deviate from the expected values, whereby an alarm signal may be triggered due to the broken glass.

According to a further aspect, a filling machine capable of providing carton-based packages enclosing liquid food is provided. The filling machine comprises a sensor arrangement according to the previous aspects.

The carton based packages, prior to filling and subsequent sealing, may be provided as open-ended bottles being transported through a sterilizing unit including a sterile gas manifold enclosing said sensor arrangement, and wherein said sterile gas manifold includes at least one sterile gas discharge spray nozzle being directed towards the open-ended bottle.

The controller of said sensor arrangement may further be configured to provide the determined concentration of substance within the sample to a sterile substance supply, whereby a feedback loop for providing the necessary substance concentration within the sample is achieved.

According to a yet further aspect, a method for determining the concentration of a substance in a sample in the presence of an interfering material by means of a sensor arrangement is provided. The method comprises the steps of providing a sensor arrangement according to the previous aspects, activating the first light source and the second light source, receiving the emitted light of said first and second wavelength being transmitted through the sample by means of the sample detector; and determining the concentration of a substance in a sample in the presence of an interfering material from at least one signal corresponding to the received emitted light.

According to another aspect, a method for controlling the concentration of a substance in a sample is provided. The method comprises the steps of providing a sample being connected to a substance supply, determining the concentration of the substance within the sample in accordance with the previous aspect, comparing the determined concentration with a reference value, determining a corrected operating parameter for said substance supply corresponding to the difference between the determined concentration and the reference value, and transmitting said corrected operating parameter to said substance supply for increasing or decreasing the concentration of the substance within the sample.

BRIEF DESCRIPTION OF DRAWINGS

These and other aspects, features and advantages of which the invention is capable of will be apparent and elucidated from the following description of embodiments of the present invention, reference being made to the accompanying drawings, in which.

DETAILED DESCRIPTION

Figure 1:
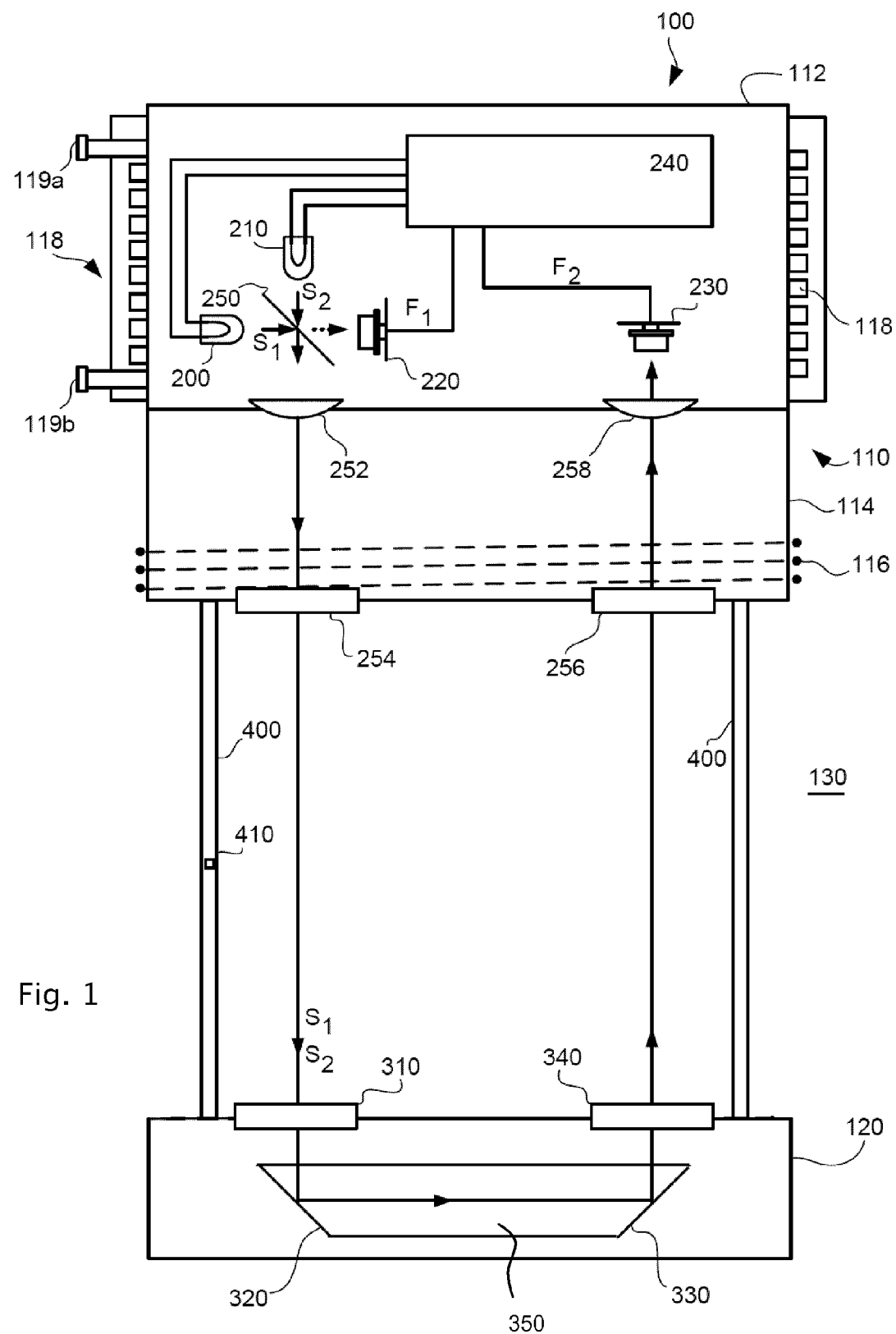
FIG. 1 is a schematic view of a sensor arrangement according to an embodiment.

Starting with FIG. 1, a schematic view of a sensor arrangement 100 is shown. The sensor arrangement 100 includes a first housing 110, a second housing 120, and a sample 130 arranged at least between the first housing 110 and the second housing 120. Preferably, the first housing 110 is connected to the second housing 120 by means of rigid supports 400.

Figure 4:
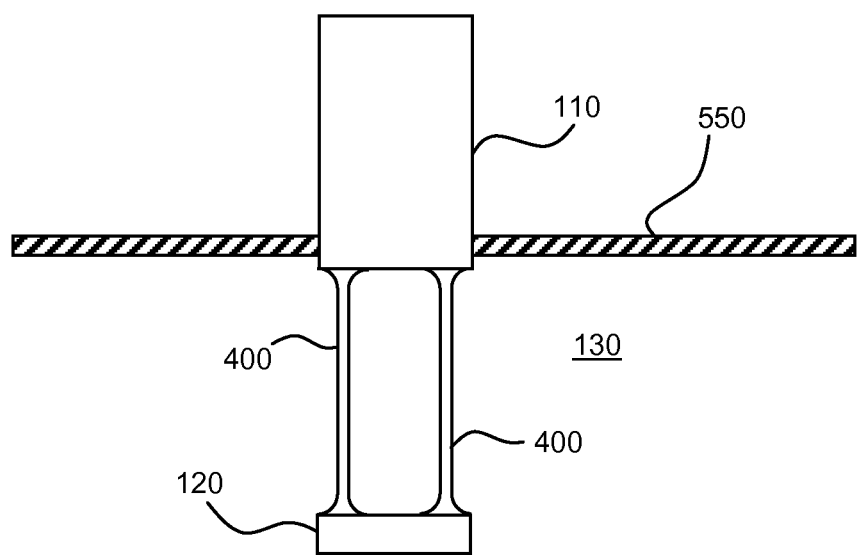
FIG. 4 is a schematic view of the sensor arrangement provided in a wall of a duct or a chamber.

The sample 130 is preferably open, i.e. the substance to be measured is allowed to flow in and out from the sample 130. Hence, in an embodiment the sensor arrangement 100 is at least partly arranged inside the sample 130 for in situ measurements of the substance(s) present in the sample 130. In a preferred embodiment, the sensor arrangement 100 is positioned relative the sample 130 such that the second housing 120 is arranged inside the sample 130, while the first housing 110 is arranged at least partly outside the sample 130. This is shown also in FIG. 4 showing the sensor arrangement 100 arranged in a wall 550 of a duct or a chamber delimiting the open sample The first housing 110 forms a closed space being sealed from the sample 130, and encloses a first light source 200, a second light source 210, a reference detector 220, and a sample detector 230. Further, a controller 240 is provided within the first housing 110 for controlling the light sources 200, 210 as well as the detectors 220, 230.

The first housing 110 is further divided into two vertically stacked compartments 112, 114. The upper compartment 112 encloses the electronic components, i.e. the controller 240, the light sources 200, 210, and the detectors 220, 230. Further, additional power supplies and/or connectors therefore are also enclosed herein.

The lower compartment 114 extends from the upper compartment 112 downwards to exit windows 254, 256. The second housing 120 is connected to the first housing 110 by means of the rigid support rods 400 extending through the sample 130.

The first light source 200 emits light $S_1$ of a first wavelength, or a first interval of wavelengths. The second light source 210 emits light $S_2$ of a second wavelength, or a second interval of wavelengths. The first wavelength, or first interval of wavelengths, is selected for being mainly absorbed by the substance present in the sample 130, as well as by other unwanted substances in the sample 130. The second wavelength, or second interval of wavelengths, is selected for being mainly transmitted through the substance present in the sample 130, but mainly absorbed by the unwanted substances in the sample 130. The unwanted substances are e.g. formed as deposits in the optical path, which will be further described below.

The first light source 200 and the second light source 210 are arranged such that the emitted light $S_1$ and $S_2$, respectively, are directed 90° relative each other. A beam splitter 250 is further provided for splitting the emitted light $S_1$, $S_2$ into two separate optical paths. The first optical path extends from the beam splitter 250 directly to the reference detector 220 whereby reference light beams, i.e. the emitted light $S_1$, $S_2$, are directly incident on the reference detector 220 without passing through the sample 130.

The second optical path extends from the beam splitter 250 to the sample detector 230 whereby sample light beams, i.e. the emitted light $S_1$, $S_2$, are incident on the sample detector 230 after passing through the sample 130.

The second optical path includes a first focusing lens 252 in order to direct the emitted light $S_1$, $S_2$ into a narrow beam. Further, the first housing 110 includes an optical exit window 254 forming an interface between the first housing 110 and the sample 130.

After passing through the sample 130 the emitted light $S_1$, $S_2$ enters the second housing 120 via an optical entry window 310 arranged to form an entry interface between the sample 130 and the second housing 120. When the light $S_1$, $S_2$ is transmitted into the second housing 120 a pair of reflectors 320, 330 are provided for redirecting the emitted light $S_1$, $S_2$ approximately 180°.

In the embodiment shown in FIG. 1 the reflectors 320, 330 are two surfaces of a retroreflector or retroflector such as a prism 350. The prism is a so called beam folding dove prism, which is shaped as a truncated right angle prism, having a first 45° angled surface 320 and a second 45° angled surface 330. In such prism the reflected light exits parallel to the input light. Within such prism total internal reflection is accomplished, and none or only small reflection losses occur between the input light and the reflected light.

The prism is arranged so that the input light is directed at right angles towards the largest rectangular surface of the prism, as seen in FIG. 1. The light is reflected internally 90 degrees at the first 45° angled surface 320 and continues to the second 45° angled surface 330 where it is reflected internally another 90 degrees where after it exits the prism. Hence, the light input and exit points of the prism are displaced from each other.

The material of the prism is preferably fused silica. A prism made of fused silica can withstand the temperature needed for sterilizing with hydrogen peroxide in gaseous phase.

Alternatively a prism made of sapphire may be used. In an alternative embodiment, the reflectors 320, 330 may be surfaces of a conventional right angle prism. In a further alternative embodiment the reflectors 320, 330 may be mirrors suitable for reflecting UV-light, such as for example UV-enhanced aluminium coated mirrors.

Hence, the light $S_1$, $S_2$ is exiting the second housing 120 at an optical exit window 340 forming an exit interface between the second housing and the sample 130 whereby it is again transmitted through the sample 130 before reentering the first housing 110 via an optical entry window 256. The sample detector 230 is arranged in the second optical path beyond a second focusing lens 258 for adjusting the shape of the transmitted light $S_1$, $S_2$.

The second optical path, i.e. the optical path through the sample 130, is thus provided as a single unique path directing both $S_1$ and $S_2$ from the beam splitter 250 to the sample detector 230.

By redirecting the light by means of the reflectors 320, 330, the total size of the sensor arrangement 100 may be decreased. However, the optical path of the light being transmitted through the sample 130 will be twice the length of the sample, whereby there is less risk that local variations in the substance concentration within the sample 130 will affect the measurements.

The reference detector 220 is preferably provided as a single detector, whereby a signal $F_1$ corresponding to the detected light is transmitted to the controller 240.

Also the sample detector 230 is preferably provided as a single detector, whereby a signal $F_2$ corresponding to the detected light is transmitted to the controller 240.

The controller 240 is thus configured to receive the signals $F_1$, $F_2$ from the detectors 220, 230 and to calculate an amount of a predefined substance present in the sample 130 while compensating for the impact of unwanted substances, i.e. interfering material, present in the second optical path. Such calculation may be done in various ways, of which at least one example is fully described in US 2003-025909 by the same applicant.

The general algorithm may however be described shortly in the following. The reference detector 220 provides a reference signal $F_1$ corresponding to the light intensity of the emitted light $S_1$, $S_2$ without passing through the sample 130. In a similar manner the sample detector 230 provides a sample signal $F_2$ corresponding to the light intensity of the emitted light $S_1$, $S_2$ after passing through the sample 130. Hence, the controller 240 receives four different light intensity values namely i) the reference intensity of $S_1$, ii) the reference intensity of $S_2$, iii) the sample intensity of $S_1$, and iv) the sample intensity of $S_2$. These light intensity values are obtained by pulsing the emitted light $S_1$ and $S_2$, and associate the respective light intensity value with its corresponding light source 200, 210. By comparing the sample intensity of $S_1$ with the reference intensity of $S_1$ a value of the total absorption by the substance present in the sample as well as by other unwanted substances in the second optical path may be obtained. Additionally, by comparing the sample intensity of $S_2$ with the reference intensity of $S_2$ a value of the absorption caused by the interfering material, i.e. the unwanted substances may be obtained. These two values may then be processed according to a predetermined formula such that concentration of the sample substance, excluding the interfering material, is obtained.

The sensor arrangement 100 may be used for determining various substances in different applications, although a preferred application is within liquid food processing technology and the determination of concentration of sterilizing agents within a food packaging material sterilization chamber. Normally such sterilization is provided by exposing the food packaging material to hydrogen peroxide gas.

In such applications it is advantageous to measure the exact concentration of hydrogen peroxide gas within the sterilization chamber due to the fact that the required concentration is of crucial importance in order to ensure the quality of the final packages, as well as the enclosed product to be distributed to consumers. In applications including gaseous hydrogen peroxide it is further necessary to avoid direct contact of the substance with the electronics of the sensor. This is provided by the sealed first housing 110 including the transmission windows 254, 256. However, using hydrogen peroxide normally also includes an addition of various stabilizers which are well known in the art. Such stabilizers tend to create deposits on contacting surfaces, including the windows 254, 256, 310, 340. These deposits may thus represent the interfering material, or unwanted substances, that are present in the optical path of the emitted light $S_1$, $S_2$. Hence, the proposed embodiments reduce the impact of such deposits when determining the actual concentration of the hydrogen peroxide.

For this particular application the first light source may be in the ultraviolet (UV) range, which light is absorbed by the hydrogen peroxide as well as the deposits formed by the stabilizers. The second light source may emit visible light which is absorbed by the interfering material, i.e. the stabilizer deposits, but transmitted through the hydrogen peroxide gas. Preferably, the first light source 200 and/or the second light source 210 include at least one light emitting diode. For detecting the amount of hydrogen peroxide the first light source 200, i.e. the UV LED, is preferably configured to emit light in the range of 220 to 300 nm, while the second light source 210, i.e. the visible light LED, is preferably configured to emit light in the range of 350 to 700 nm.

Additional features are also available in the sensor arrangement 100 for providing more efficient and robust measurements of the concentration of substances in the sample.

In a particular embodiment, a temperature sensor 410 is arranged on the support rods 400. The support 400 may e.g. be formed as a plurality of rods securely fixating the second housing 120 to the first housing 110. The rods may be separated from each other in order to allow substance within the sample 130 to flow through. In an embodiment, the first housing 110 and the second housing 120 are formed as cylinders, whereby the ribs are provided at the periphery of the opposing ends. By measuring the temperature of the sample 130 it is possible to determine the actual substance concentration more accurately, since the absorption is a function of the amount of substance. However, concentration depends not only on quantity but also on pressure and temperature, why an additional temperature sensor 410 allows a more precise determination of the concentration for a given pressure. For this purpose the temperature sensor 410 is connected to the controller 240, either directly or remotely.

Further to this, the lower compartment 114 of the first housing 110 includes a heater 116 which is configured to increase the temperature of the windows 254, 256 of the first housing 110. The heater 116 may be provided as a heating coil surrounding the lower compartment 114, although other heating devices may also be utilized for the specific application.

The heater 116 provides a number of advantages depending on the choice of substance within the sample 130. If the substance is gaseous hydrogen peroxide the heater will reduce the risk of condensation on the windows 254, 256. Since condensation may lead to a change in absorbance of the emitted light improved measurements are provided as the risk of condensation is reduced, or even eliminated. Further, by heating the windows 254, 256 there is less risk of deposit formation due to the presence of the hydrogen peroxide stabilizers and their ability to deposit on cold surfaces.

Additionally, the first housing 110 may include a cooler 118 for reducing the temperature within the first housing 110. By reducing the temperature, the operation of the electronic components, such as the light sources 200, 210 and the detectors 220, 230 is improved. The cooler may be provided as a closed system of channels surrounding the inner housing 110, whereby cooling fluid, such as cold water, enters the system of channels at an inlet 119a and exits at an outlet 119b. For additional cooling efficiency a fan may be provided inside the first housing 110 for circulating the air within the first housing 110.

Preferably, the controller 240 receives a signal from a further temperature sensor arranged within the first housing 110 such that the temperature of the electronic components may be monitored continuously during operation. Also, a feedback loop may be implemented by means of the controller 240 such that the flow of cooling fluid may be increased upon an excess temperature within the first housing 110. In the event that the temperature exceeds a stored reference temperature the controller is adapted to switch off the light sources 200, 210. The stored reference temperature is 45° C., but could of course be set to another temperature value. In case of a high temperature the controller 240 may in addition, or as an alternative, switch off the heater 116.

The described measures are taken in order to increase the lifetime of the LEDs, especially the UV-LED.

So far, the reference detector 220 and the sample detector 230 are provided as single detectors receiving the emitted light $S_1$, $S_2$. However, each one of these detectors 220, 230 may also be provided as two separate detectors, wherein each detector is configured to detect only one of the emitted wavelengths or interval of wavelengths.

However, in FIG. 1 a preferred configuration is illustrated in which the reference detector 220, as well as the sample detector 230, is provided as a single detector capable of detecting the entire emitted light, i.e. both $S_1$ and $S_2$. In order to separate $S_1$ and $S_2$ from each other in a robust manner the controller 240 is controlling the light sources 200, 210 in a pulsed manner.

Figure 2:
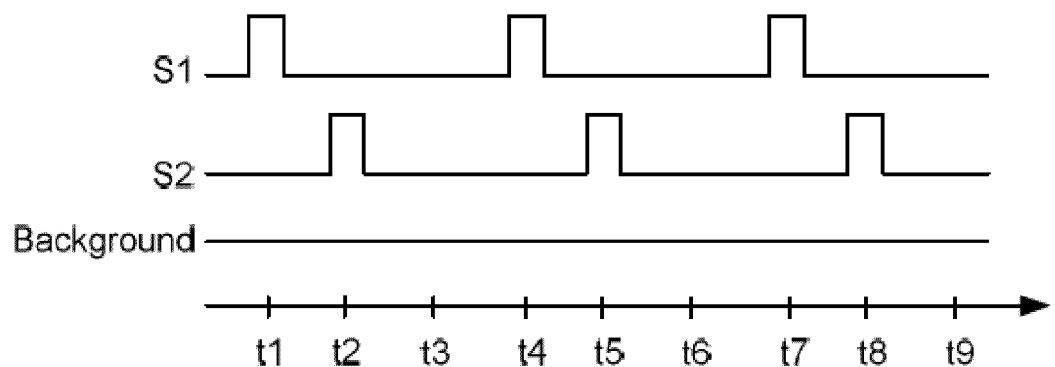
FIG. 2 is a diagram showing the sensor arrangement detecting sequence according to an embodiment.

Starting at t1, see FIG. 2, the controller 240 activates the first light source 200 for a short period of time, corresponding to a light pulse $S_1$ of the first wavelength or interval of wavelengths. As the detectors 220, 230 are configured for continuous operation, they will sense the emitted light $S_1$ however not knowing from which light source 200, 210 it has been emitted. Since the controller 240 has triggered the light source 200 it may associate the detected signals with the correct light source 200. In a next step, at t2, the controller activates the second light source 210 for a short period of time. Instantly, the controller associates the detected signals with the second light source 210. At this point the controller 240 is capable of determining the amount of substance being present in the sample 130 while compensating for any unwanted interfering material. However, the quantification of substance may be further improved by the provision of a third detection sample at t3. Since none of the light sources 200, 210 have been activated the detected signals thus corresponds to background radiation affecting the previously determined absorbance and/or transmittance. Hence, the intensity being detected at t3 may be subtracted from the previous detected signals at t1 and t2, respectively. This procedure is preferably repeated during operation of the equipment having the sensor arrangement 100 installed to it, which repetition is illustrated as t4-t9. The embodiment where background light is measured is particularly advantageous in application such as food processing, where background light may be of the same wavelength as the first and/or second wavelength. For example, a sterilizing chamber in a filling machine may be exposed to light from the outside, i.e. normal room lightning. This light may thus overlap the second wavelength, being in the visible range, why a reduction of such background light will improve the operation and reliability of the sensor arrangement.

Pulsing the light reduces the time the UV-LED is in operation, which increases the lifetime of the UV-LED.

The controller 240 may further be connected to a memory storing reference values for the received detector signal. Such reference values may represent normal operation conditions, whereby the controller 240 may further be configured to trigger an alarm if the detected signals deviate from the stored reference values. This may be particular advantageous in cases where the conditions in the sample may damage the equipment, such as the windows 254, 256, 310, 340. If e.g. one of the windows 254, 256, 310, 340 will be broken the light intensity of the detected signals $F_1$, $F_2$ will differ from the expected values why an alarm, indicating service or support, may be generated.

The memory is also for example storing reference values for the efficiency of the light sources as a function of temperature. The controller is configured to transmit an alarm signal if a received detector signal of the sample detector (230), associated to the detected temperatures of the first and second light sources 200, 210, is significantly lower than the stored reference values.

Figure 3:
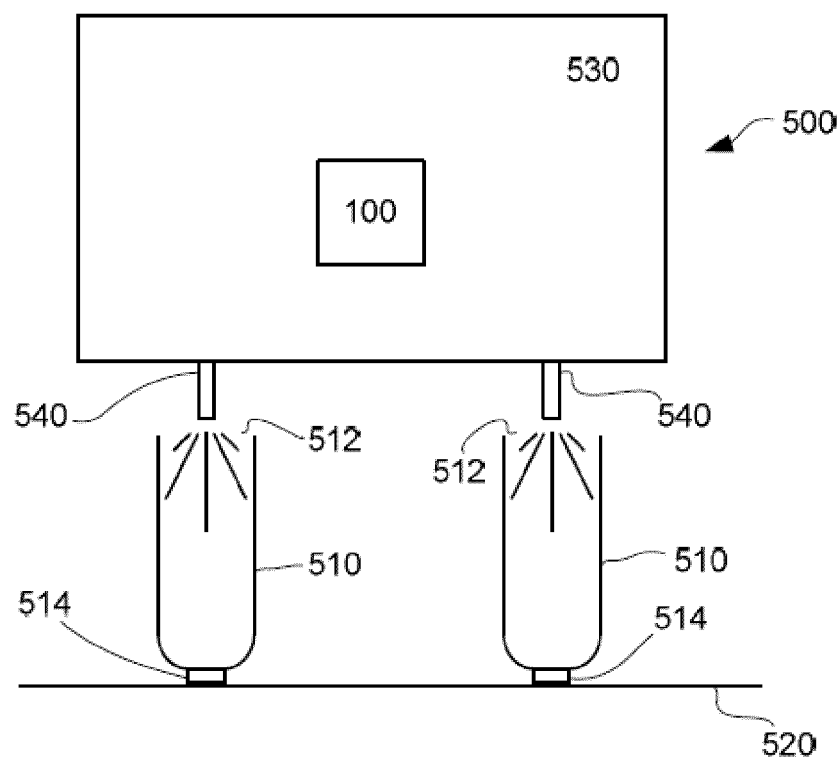
FIG. 3 is a schematic side view of a part of a filling machine including a sensor arrangement.

Now turning to FIG. 3, an industrial application of the sensor arrangement 100 is shown. A part of a filling machine is illustrated as a sterilization unit 500 in which ready-to-fill packages 510 are introduced by means of a carrier 520. The packages 520 have previously, preferably within an upstream section of the same filling machine 500, been semi-folded to form carton-based sleeves having one open end 512 and one closed end 514. The closed end 514, e.g. provided by a plastic assembly comprising a neck, shoulder, and cap sealing the pouring spout may e.g. have been injected molded to the carton-based laminate forming the sleeve.

The sterilization unit 500 includes a sterile gas manifold 530 enclosing the gaseous sterilization substance (e.g. $H_2O_2$ with or without added stabilizers) and comprises a number of discharge nozzles 540 configured to eject a spray distribution of the sterilization substance to the interior of the packages 510.

The sensor arrangement 100 is arranged within the manifold 530 for measuring and determining the concentration of the sterilization substance. Hence, the sample 130 of the sensor arrangement corresponds to the interior of the manifold 530, while at least the first housing 110 is sealed from the sterilization substance. The sensor arrangement 100 is therefore configured to operate continuously during operation of the filling machine in order to accurately determine the quality and robustness of the sterilization unit 500. Preferably, the sensor arrangement 100 is capable of returning the determined amount of substance within the sample 130 to a substance supply (not shown) for increasing or decreasing the amount of substance within the manifold 530, i.e. the sample 130.

Such feed-back loop may be implemented in various applications, whereby a determined concentration is compared with a reference value corresponding to a desired concentration. The difference between the determined concentration and the reference value may thus be converted to a corrected operating parameter, such as flow rate, of a substance supply being connected to the sample. Hence, the controller of the sensor arrangement may thus be configured to transmit a signal to the substance supply in order to increase or decrease the concentration of the substance within the sample.

Although specific embodiments have been described it should be appreciated that various modifications may be made to the printing systems without departing from the scope as defined in the accompanying claims.

The invention claimed is:

1. A sensor arrangement for determining a concentration of a substance in a sample in the presence of an interfering material, comprising:

a first light source emitting light in a pulsed manner at a first wavelength to be absorbed by the substance, a second light source emitting light in a pulsed manner at a second wavelength to be transmitted through the substance, at least one optical device configured to direct, at least a part of the emitted pulsed light of the first wavelength and at least a part of the emitted pulsed light of the second wavelength, through the sample along the same optical path in a sequential order, and a sample detector arranged in the optical path in order to receive the emitted pulsed light of the first and second wavelengths transmitted through the sample, wherein the sample detector is configured to detect the emitted pulsed light of the first wavelength during a first period of time and detect the emitted pulsed light of the second wavelength during a second period of time following the first period of time, wherein the interfering material is formed as deposits on one or more of the at least one optical device that is exposed to the substance, and wherein the first wavelength and the second wavelength are absorbed by the interfering material.

2. The sensor arrangement of claim 1, wherein the first light source, the second light source, and the sample detector are arranged on one side of the sample.

3. The sensor arrangement of claim 2, wherein the at least one optical device includes a plurality of reflectors arranged on another side of the sample, the plurality of reflectors together being adapted to re-direct the emitted pulsed light of the first and second wavelengths to the sample detector.

4. The sensor arrangement of claim 3, wherein the plurality of reflectors are surfaces of a retroreflector prism in which reflection is achieved by total internal reflection.

5. The sensor arrangement according to claim 1, further comprising a reference detector configured to receive a part of the emitted pulsed light of the first and second wavelengths not being transmitted through the sample.

6. The sensor arrangement according to claim 5, wherein the reference detector is arranged on the same side of the sample as the first light source, the second light source, and the sample detector.

7. The sensor arrangement according to claim 6, wherein the first light source, the second light source, the sample detector, and the reference detector are enclosed in a housing sealed from the sample.

8. The sensor arrangement according to claim 7, wherein the housing comprises a first optical window configured to allow light emitted from the first light source and the second light source to exit the housing and enter the sample, and a second optical window configured to allow the light emitted from the first light source and the second light source to exit the sample and enter the housing, wherein the sensor arrangement further comprises a heater configured to increase a temperature of the first and second optical window.

9. The sensor arrangement according to claim 7, wherein the housing includes a cooler for reducing a temperature within the housing.

10. The sensor arrangement according to claim 5, further comprising a controller being connected to the first light source, the second light source, the sample detector, and the reference detector and being configured to activate the first light source and the second light source in the pulsed manner, the controller being further configured to associate a received signal of the sample detector and the reference detector with the associated light source.

11. The sensor arrangement according to claim 10, wherein the controller is further configured to associate the received signal of the sample detector and the reference detector as background light at occasions where none of the first light source and the second light source is activated.

12. The sensor arrangement according to claim 10, wherein the controller is configured to control a temperature of the first light source and the second light source, and to switch off the associated light source if the temperature exceeds a stored reference temperature.

13. The sensor arrangement according to claim 10, wherein the controller is connected to a memory storing reference values for the received detector signals, and wherein the controller is further configured to transmit an alarm signal if one of the received detector signals differs from the stored reference values.

14. The sensor arrangement according to claim 1, wherein the first light source is a UV-LED.

15. A filling machine capable of providing carton-based packages enclosing liquid food, comprising a sensor arrangement according to claim 1.

16. The filling machine according to clam 15, wherein the carton-based packages, prior to filling and subsequent sealing, are provided as open-ended bottles being transported through a sterilizing unit including a sterile gas manifold enclosing the sensor arrangement, and wherein the sterile gas manifold includes at least one sterile gas discharge spray nozzle being directed towards the open-ended bottle.

17. The filling machine according to claim 16, wherein the controller of the sensor arrangement is configured to provide the determined concentration of substance within the sample to a sterile substance supply.

18. A method for controlling a concentration of a substance in a sample, comprising:
providing a sample being connected to a substance supply,
determining the concentration of the substance within the sample in accordance with claim 16,
comparing, via a controller associated with the sensor arrangement, the determined concentration with a reference value,
determining, via the controller, a corrected operating parameter for the substance supply corresponding to the difference between the determined concentration and the reference value, and
transmitting, via the controller, the corrected operating parameter to the substance supply for increasing or decreasing the concentration of the substance within the sample.

19. A method for determining a concentration of a substance in a sample in the presence of an interfering material, via the sensor arrangement according to claim 1, the method comprising:
activating the first light source and the second light source,
receiving the emitted pulsed light of the first and second wavelengths being transmitted through the sample via the sample detector; and
determining the concentration of the substance in the sample in the presence of the interfering material from at least one signal corresponding to the received emitted pulsed light.

* * * * *